United States Patent
Sawhney

(10) Patent No.: US 9,254,267 B2
(45) Date of Patent: Feb. 9, 2016

(54) COMPOSITE HYDROGEL DRUG DELIVERY SYSTEMS

(75) Inventor: Amarpreet S. Sawhney, Lexington, MA (US)

(73) Assignee: Incept, LLC, Lexington, MA (US)

(*) Notice: Subject to any disclaimer, the term of this patent is extended or adjusted under 35 U.S.C. 154(b) by 2220 days.

(21) Appl. No.: 12/218,152

(22) Filed: Jul. 11, 2008

(65) Prior Publication Data

US 2008/0279944 A1    Nov. 13, 2008

Related U.S. Application Data

(60) Division of application No. 10/639,700, filed on Aug. 12, 2003, now Pat. No. 7,413,752, which is a continuation of application No. 09/134,287, filed on Aug. 14, 1998, now Pat. No. 6,632,457.

(51) Int. Cl.
| | |
|---|---|
| *A61K 9/16* | (2006.01) |
| *A61K 9/51* | (2006.01) |
| *A61K 9/20* | (2006.01) |
| *A61K 51/12* | (2006.01) |

(52) U.S. Cl.
CPC ............. *A61K 9/1647* (2013.01); *A61K 9/167* (2013.01); *A61K 9/2077* (2013.01); *A61K 51/1213* (2013.01)

(58) Field of Classification Search
None
See application file for complete search history.

(56) References Cited

U.S. PATENT DOCUMENTS

| | | | |
|---|---|---|---|
| 3,161,602 | A | 12/1964 | Herbig et al. |
| 3,242,237 | A | 3/1966 | Belak et al. |
| 3,423,489 | A | 1/1969 | Arens et al. |
| 3,640,741 | A | 2/1972 | Etes |
| 3,779,942 | A | 12/1973 | Bolles |
| 3,833,003 | A | 9/1974 | Taricco |
| 3,865,108 | A | 2/1975 | Hartop |
| 3,949,073 | A | 4/1976 | Daniels et al. |
| 3,975,350 | A | 8/1976 | Hudgin et al. |
| 3,991,766 | A | 11/1976 | Schmitt et al. |
| 3,992,562 | A | 11/1976 | Denzinger et al. |

(Continued)

FOREIGN PATENT DOCUMENTS

| | | |
|---|---|---|
| CS | 144720 * | 7/1972 |
| EP | 0443743 B1 | 5/1991 |

(Continued)

OTHER PUBLICATIONS

AS Sawhney, CP Pathak, JA Hubbell. "Bioerodible Hydrogels Based on Photopolymerized Poly(ethylene glycol)-co-poly(alpha-hydroxy acid) Diacrylate Macromers." Macromolecules, vol. 26, 1993, pp. 581-587.*

(Continued)

*Primary Examiner* — Isaac Shomer
(74) *Attorney, Agent, or Firm* — Dardi & Herbert, PLLC; Curtis B. Herbert

(57) ABSTRACT

Compositions and methods are provided to control the release of relatively low molecular weight therapeutic species through hydrogels by first dispersing or dissolving such therapeutic species within relatively hydrophobic rate modifying agents to form a mixture. The mixture is formed into microparticles that are dispersed within bioabsorbable hydrogels, so as to release the water soluble therapeutic agents in a controlled fashion. Methods of using the compositions of the present invention in therapeutic systems are also provided.

25 Claims, 1 Drawing Sheet

(56) References Cited

U.S. PATENT DOCUMENTS

| | | |
|---|---|---|
| 4,002,173 A | 1/1977 | Manning et al. |
| 4,014,335 A | 3/1977 | Arnold |
| 4,101,380 A | 7/1978 | Rubinstein et al. |
| 4,107,288 A | 8/1978 | Oppenheim et al. |
| 4,141,973 A | 2/1979 | Balazs |
| 4,150,114 A * | 4/1979 | Smith ............... 424/60 |
| 4,195,129 A | 3/1980 | Fukui et al. |
| 4,207,893 A | 6/1980 | Michaels |
| 4,247,406 A | 1/1981 | Widder et al. |
| 4,311,146 A | 1/1982 | Wonder |
| 4,507,466 A | 3/1985 | Tomalia et al. |
| 4,530,840 A | 7/1985 | Tice et al. |
| 4,532,134 A | 7/1985 | Malette et al. |
| 4,568,737 A | 2/1986 | Tomalia et al. |
| 4,597,970 A | 7/1986 | Sharma et al. |
| 4,631,188 A | 12/1986 | Stoy et al. |
| 4,693,887 A | 9/1987 | Shah |
| 4,740,534 A | 4/1988 | Matsuda et al. |
| 4,741,872 A | 5/1988 | DeLuca et al. |
| 4,804,691 A | 2/1989 | English et al. |
| 4,826,945 A | 5/1989 | Cohn et al. |
| 4,828,857 A | 5/1989 | Sharma et al. |
| 4,839,345 A | 6/1989 | Doi et al. |
| 4,911,926 A | 3/1990 | Henry et al. |
| 4,925,677 A | 5/1990 | Feijen |
| 4,938,763 A | 7/1990 | Dunn et al. |
| 4,979,959 A | 12/1990 | Guire |
| 4,994,277 A | 2/1991 | Higham et al. |
| 5,041,292 A | 8/1991 | Feijen |
| 5,093,319 A | 3/1992 | Higham et al. |
| 5,122,614 A | 6/1992 | Zalipsky |
| 5,126,141 A | 6/1992 | Henry |
| 5,143,662 A | 9/1992 | Chesterfield et al. |
| 5,152,782 A | 10/1992 | Kowligi et al. |
| 5,160,745 A | 11/1992 | DeLuca et al. |
| 5,167,624 A | 12/1992 | Butler et al. |
| 5,171,148 A | 12/1992 | Wasserman et al. |
| 5,198,220 A | 3/1993 | Damani |
| 5,213,580 A | 5/1993 | Slepian et al. |
| 5,232,984 A | 8/1993 | Hubbell et al. |
| 5,266,326 A | 11/1993 | Barry et al. |
| 5,278,202 A | 1/1994 | Dunn et al. |
| 5,296,228 A | 3/1994 | Chang et al. |
| 5,304,147 A | 4/1994 | Johnson et al. |
| 5,306,500 A | 4/1994 | Rhee et al. |
| 5,330,768 A | 7/1994 | Park et al. |
| 5,366,498 A | 11/1994 | Brannan et al. |
| 5,376,375 A | 12/1994 | Rhee et al. |
| 5,380,536 A | 1/1995 | Hubbell et al. |
| 5,385,561 A | 1/1995 | Cerny |
| 5,410,016 A | 4/1995 | Hubbell et al. |
| 5,446,090 A | 8/1995 | Harris |
| 5,462,976 A | 10/1995 | Matsuda et al. |
| 5,468,811 A | 11/1995 | Moro et al. |
| 5,509,899 A | 4/1996 | Fan et al. |
| 5,514,379 A | 5/1996 | Weissleder et al. |
| 5,514,380 A | 5/1996 | Song et al. |
| 5,529,914 A | 6/1996 | Hubbell et al. |
| 5,565,215 A * | 10/1996 | Gref et al. ............ 424/501 |
| 5,573,934 A | 11/1996 | Hubbell et al. |
| 5,583,114 A | 12/1996 | Barrows et al. |
| 5,587,175 A | 12/1996 | Viegas et al. |
| 5,588,960 A | 12/1996 | Edwards et al. |
| 5,589,194 A | 12/1996 | Tsuei et al. |
| 5,612,050 A | 3/1997 | Rowe et al. |
| 5,618,563 A | 4/1997 | Berde et al. |
| 5,622,725 A * | 4/1997 | Kross ............... 424/665 |
| 5,624,840 A | 4/1997 | Naughton et al. |
| 5,626,863 A * | 5/1997 | Hubbell et al. ........ 424/426 |
| 5,631,329 A | 5/1997 | Yin et al. |
| 5,650,173 A | 7/1997 | Ramstack et al. |
| 5,650,450 A | 7/1997 | Lovette et al. |
| 5,660,849 A | 8/1997 | Polson et al. |
| 5,665,063 A | 9/1997 | Roth et al. |
| 5,702,716 A | 12/1997 | Dunn et al. |
| 5,723,269 A | 3/1998 | Akagi et al. |
| 5,731,005 A | 3/1998 | Ottoboni et al. |
| 5,744,545 A | 4/1998 | Rhee et al. |
| 5,752,974 A | 5/1998 | Rhee et al. |
| 5,773,025 A | 6/1998 | Baichwal |
| 5,800,841 A | 9/1998 | Miyajima |
| 5,807,581 A | 9/1998 | Rosenblatt et al. |
| 5,820,882 A | 10/1998 | Hubbell et al. |
| 5,834,274 A | 11/1998 | Hubbell et al. |
| 5,837,226 A | 11/1998 | Jungherr et al. |
| 5,849,412 A | 12/1998 | Bromberg et al. |
| 5,858,746 A | 1/1999 | Hubbell et al. |
| 5,874,500 A | 2/1999 | Rhee et al. |
| 5,932,462 A | 8/1999 | Harris et al. |
| 5,985,177 A | 11/1999 | Yoshida et al. |
| 5,986,043 A | 11/1999 | Hubbell et al. |
| 6,129,761 A | 10/2000 | Hubbell et al. |
| 6,153,211 A | 11/2000 | Hubbell et al. |
| 6,156,345 A | 12/2000 | Chudzik et al. |
| 6,162,241 A | 12/2000 | Coury et al. |
| 6,171,600 B1 | 1/2001 | Dahms |
| 6,201,065 B1 | 3/2001 | Pathak et al. |
| 6,214,966 B1 | 4/2001 | Harris |
| 6,261,544 B1 | 7/2001 | Coury et al. |
| 6,290,729 B1 | 9/2001 | Slepian et al. |
| 6,352,682 B2 | 3/2002 | Leavitt et al. |
| 6,517,824 B1 | 2/2003 | Kohn et al. |
| 6,639,014 B2 | 10/2003 | Pathak et al. |
| 6,833,408 B2 | 12/2004 | Sehl et al. |
| 6,887,974 B2 | 5/2005 | Pathak |
| 6,962,979 B1 | 11/2005 | Rhee |

FOREIGN PATENT DOCUMENTS

| | | |
|---|---|---|
| EP | 1 704 878 A2 | 9/2006 |
| JP | 09-255562 | 9/1997 |
| WO | WO 90/02133 A1 | 3/1990 |
| WO | WO 94/25080 A1 | 11/1994 |
| WO | 9515143 A2 | 6/1995 |
| WO | 9705185 A2 | 2/1997 |
| WO | 9719973 A1 | 6/1997 |
| WO | WO 97/22371 A1 | 6/1997 |
| WO | 9903454 A1 | 1/1999 |
| WO | 9962510 A2 | 12/1999 |

OTHER PUBLICATIONS

English Abstract of Novak et al., CS 144720. Patent was issued in 1974. Abstract is 1 page.*

Abuchowski et al., "Cancer Therapy with Chemically Modified Enzymes. I. Antitumor Properties of Polyethylene Glycol-Asparaginase Conjugates," Cancer Biochem. Biophys., 7:175-186 (1984).

Bailey et al., "Synthesis of Polymerized Vesicles with Hydrolyzable Linkages," Macromolecules, 25:3-11 (1992).

Bhatia et al., "The Effect of Site Implantation and Animal Age on Properties of Polydioxanone Pins," J. Biomater. Sci., Polymer Edn., Bamford, C.H. et al., eds., 6(5):435-446 (1994).

Dong et al., "Dextran Permeation Through Poly (N-Isopropylacrylamide) Hydrogels," J. Biomater. Sci., Polymer Edn., Bamford, C.H. et al., eds., 5(5):473-484 (1994).

Edgington et al., "New Horizons for Stem-Cell Bioreactors," Bio/Technology, 10:1099-1106 (1992).

Jarrett et al, "Bioabsorbable Hydrogel Tissue Barrier: In Situ Gelation Kinetics," Soc. for Biomater., Transactions of 21st Annual Meeting: 182 (1995).

Klibanov et al., "Activity of Amphipathic Poly (ethylene glycol) 5000 to Prolong the Circulation Time of Liposomes Depends on the Liposome Size and is Unfavorable for Immunoliposome Binding to Target," Biochimica et Biophysica Acta, 1062:142-148 (1991).

Lasic et al., "Sterically Stabilized Liposomes: A Hypothesis on the Molecular Origin of the Extended Circulation Times," Biochimica et Biophysica Acta, 1070:187-192 (1991).

(56) References Cited

OTHER PUBLICATIONS

Ley et al., "Endothelial, Not Hemodynamic, Differences are Responsible for Preferential Leukocyte Rolling in Rat Mesenteric Venules," Circulation Research, 69(4):1034-1041 (1991).

Mayhew et al., "Characterization of Liposomes Prepared by Using a Microemulsifier," Biochimica et Biophysica Acta, 775:169-174 (1984).

Nagaoka et al., "Interaction Between Blood Components and Hydrogels with Poly(oxyethylene) Chains," Polymers as Biomaterials, Shalaby, S.W. et al., eds., Plenum Press, New York, 361-374 (1984).

Park et al., Biodegradable Hydrogels for Drug Delivery, Technomic Publishing Co., Inc., Lancaster, PA (1993).

Park, "Enzyme-Digestible Swelling Hydrogels as Platforms for Long-Term Oral Drug Delivery: Synthesis and Characterization," Biomaterials, 9:435-441 (1988).

Raud et al., "Leukocyte Rolling and Firm Adhesion in the Microcirculation," Gastroenterology, 104:310-314 (1993).

Remington's Pharmaceutical Sciences, 14th Ed., J.E. Hoover et al., eds., Mack Publishing Co., Easton, Pennsylvania (1970).

Sawhney et al., "Bioerodible Hydrogels Based on Photopolymerized Poly(ethylene glycol)-co-poly($\alpha$-hydroxy acid) Diacrylate Macromers," Macromolecules, 26:581-587 (1993).

Shalaby et al., "In Vitro and In Vivo Studies of Enzyme-Digestible Hydrogels for Oral Drug Delivery," J. Controlled Release, 19:131-144 (1992).

Shalaby, "Bioabsorbable Polymers," Encyclopedia of Pharmaceutical Technology, Swarbrick, J. et al., eds., Marcel Dekker, Inc., New York, 1:465-476 (1988).

Silberberg, "Network Deformation in Flow," Molecular Basis of Polymer Networks, Baumgartner, A. et al., eds., Springer-Verlag, Berlin, 42:147-151 (1989).

Smith et al., "Association Reactions for Poly(alkylene Oxides) and Polymeric Poly (carboxylic Acids)," Ind. Eng. Chem., 51(11):1361-1364 (1959).

Torchilin et al., "Liposome-Polymer Systems. Introduction of Liposomes into a Polymer Gel and Preparation of the Polymer Gel Inside a Liposome," Polymer Sci. U.S.S.R., 30(10): 2307-2312 (1988).

Zalipsky et al., "Esterification of Polyethylene Glycols," J. Macromol. Sci.-Chem., A21 (6&7): 839-845 (1984).

\* cited by examiner

COMPOSITE HYDROGEL DRUG DELIVERY SYSTEMS

RELATED APPLICATION

The application is a divisional of U.S. Ser. No. 10/639,700 filed Aug. 12, 2003, now U.S. Pat. No. 7,413,752 which is a continuation of U.S. patent application Ser. No. 09/134,287 filed Aug. 14, 1998, now U.S. Pat. No. 6,632,457 which are hereby incorporated herein by reference.

FIELD OF THE INVENTION

The present invention relates to compositions and methods for providing controlled release of therapeutic species using hydrogels.

BACKGROUND OF THE INVENTION

For a drug to be effective, a certain concentration level (called the therapeutic index) must be maintained for a certain period of time, at specific location(s). Systemically administered drugs accomplish the first two objectives, but in an inefficient fashion and with the potential for toxic side effects at high doses. Systemic administration of controlled release formulations accomplish these two objectives with a more efficient utilization of the drug and may reduce side effects. Local implantation of drug delivery systems may further improve the efficiency of drug utilization.

Hydrogels are materials that absorb solvents (such as water), undergo rapid swelling without discernible dissolution, and maintain three-dimensional networks capable of reversible deformation. Hydrogels may be uncrosslinked or crosslinked. Uncrosslinked hydrogels are able to absorb water but do not dissolve due to the presence of hydrophobic and hydrophilic regions. Covalently crosslinked networks of hydrophilic polymers, including water soluble polymers, are traditionally denoted as hydrogels in the hydrated state. A number of aqueous hydrogels have been used in various biomedical applications, such as, for example, soft contact lenses, wound management, and drug delivery.

Hydrogels can be formed from natural polymers such as glycosaminoglycans and polysaccharides, proteins, etc., where the term "glycosaminoglycan" encompasses complex polysaccharides that are not biologically active (i.e., not compounds such as ligands or proteins) and have repeating units of either the same saccharide subunit or two different saccharide subunits. Some examples of glycosaminoglycans include dermatan sulfate, hyaluronic acid, the chondroitin sulfates, chitin, heparin, keratin sulfate, keratosulfate, and derivatives thereof.

Glycosaminoglycans may be extracted from a natural source, purified and derivatized, or synthetically produced or synthesized by modified microorganisms such as bacteria. These materials may also be modified synthetically from a naturally soluble state to a partially soluble or water swellable or hydrogel state. This can be done, for example, by conjugation or replacement of ionizable or hydrogen bondable functional groups such as carboxyl and/or hydroxyl or amine groups with other more hydrophobic groups.

Hydrophilic polymeric materials suitable for use in forming hydrogels include poly(hydroxyalkyl methacrylate), poly(electrolyte complexes), poly(vinylacetate) cross-linked with hydrolyzable bonds, water-swellable N-vinyl lactams polysaccharides, natural gum, agar, agarose, sodium alginate, carrageenan, fucoidan, furcellaran, laminaran, hypnea, eucheuma, gum arabic, gum ghatti, gum karaya, gum tragacanth, locust beam gum, arabinogalactan, pectin, amylopectin, gelatin, hydrophilic colloids such as carboxymethyl cellulose gum or alginate gum cross-linked with a polyol such as propylene glycol, and the like. Several formulations of previously known hydrogels are described in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold, U.S. Pat. No. 4,207,893 to Michaels, and in *Handbook of Common Polymers*, (Scott and Roff, Eds.) Chemical Rubber Company, Cleveland, Ohio.

Synthesis and biomedical and pharmaceutical applications of absorbable or biodegradable hydrogels based on covalently crosslinked networks, comprising polypeptide or polyester components as the enzymatically or hydrolytically labile components, respectively, have been described by a number of researchers. See, e.g., Jarrett, et al., "Bioabsorbable Hydrogel Tissue Barrier: In Situ Gelation Kinetics", *Trans. Soc. Biomater.*, Vol. XVIII, 182, 1995 and Park, "Enzyme-digestible Swelling Hydrogels as Platforms for Long-term Oral Drug Delivery: Synthesis and Characterization", *Biomaterials*, 9:435 (1988).

The hydrogels most often cited in the literature are those made of water soluble polymers, such as polyvinyl pyrrolidone, which have been crosslinked with naturally derived biodegradable components such as those based on albumin. Totally synthetic hydrogels that have been studied for controlled drug release, and as membranes for the treatment of post-surgical adhesion, are based on covalent networks formed by the addition polymerization of acrylic-terminated, water soluble chains of polyether dipolylactide block copolymers.

Bioabsorbable hydrogels are well suited for local implantation, but relatively low molecular weight molecules are rapidly released from hydrogels due to the relatively open networks of previously known hydrogels. Relatively low molecular weight compounds, however, constitute a vast majority of therapeutic molecules and drugs. Controlled drug delivery from implantable and bioabsorbable devices has been the subject of extensive exploration, but no suitable absorbable systems are known that are capable of delivering both water soluble and water insoluble relatively low molecular weight drugs.

The development of compositions and methods to provide controlled release delivery of relatively low molecule weight drugs presents the following challenges: the delivery matrix needs to be safe and absorbable; drug release should be controlled and sustained, while being free from "burst effects"; and the devices should be simple to fabricate so as to prevent denaturation of sensitive entrapped drugs.

Previously known methods and compositions for providing sustained controlled release of therapeutic species, and applications suitable for use of such compositions and methods, are discussed hereinbelow, and include: (a) microencapsulation and (b) targeted microspheres.

a. Microencapsulation

Several previously known delivery systems employ biodegradable microspheres and/or microcapsules that include biodegradable polymers, such as poly d, l-lactic acid (PLA) and copolymers of lactic acid and glycolic acid (PLGA). These polymers are most widely used in sustained release devices, and may be obtained by polycondensation of lactic acid or glycolic acid in the presence or absence of a catalyst or other activator. Microcapsules prepared from such materials may be administered intramuscularly or by other parenteral routes.

The water solubility of a number of biologically active molecular compounds, however, has proven to be a limiting factor in optimizing molecular compound loading efficiency in biodegradable microspheres and/or microcapsules. Specifically, it has been observed that the loading efficiency of water soluble drugs into, for example, PLA or PLGA-polymeric microspheres, is relatively low when conventional oil/water systems are used in a solvent evaporation process. This has been attributed to the observation that such drugs readily diffuse into the aqueous outer phase of the emulsion system.

Most of the microspheres described in the literature belong to the class of "matrix-type" drug delivery capsules, in which the "foreign" (i.e. drug) particles are dispersed homogeneously in direct contact with the polymer. The process of manufacturing such capsules also frequently involves direct contact between the drug and a polymer solvent, such as acetonitrile or methylene chloride. Such contact between the biologically active molecule and the polymer, polymer solvent or enzymes in the biological system may promote degradation of the intended pharmaceutical.

Specifically, the monomer and dimer residues in the polymer may degrade the protein, and direct contact between the polymer and proteins and enzymes may result in polymeric degradation over time. Previously known techniques to encapsulate peptides in biodegradable polymers typically utilize a solvent-nonsolvent system. Such systems often produce high solvent residuals, poor content uniformity of the peptide in the microspheres, and instability due to the contact of the biological agent with the polymer, organic solvent (e.g. methylene chloride, acetonitrile), and some cases, a surfactant.

To address the use of organic solvents that may have a potentially detrimental effect on entrapped substances, and which complicate processing, several alternate methods have been proposed. U.S. Pat. No. 5,589,194 to Tsuei et al. describes preparation of microcapsules by dispersing or dissolving an active component in a solid matrix-forming material that has been thermally softened to form an encapsulation composition. The encapsulation composition is injected as an intact stream into a quenching liquid to provide solid microcapsules.

U.S. Pat. No. 3,242,237 to Belak et al. describes a process for forming discrete slow release fertilizer particles, wherein solid fertilizer is dispersed in melted wax and dropped into water in the form of droplets. The droplets solidify in particle form upon contact with the water, and are separated from the water.

European Patent application 0 443 743 to Kubota discloses a method to encapsulate particulate Vitamin C in fine lipid powders by ringing a particulate core containing Vitamin C into colliding contact with particles of a coating material composed on one or more fine powdery lipids. The lipids form a coating of agglomerated particles that surround the particulate core.

U.S. Pat. No. 3,161,602 to Herbig discloses a process for making capsules utilizing a three-phase system: a wax-like wall material, a nucleus material, and a substantially inert oily vehicle. The waxy material is melted to a liquid and agitated to coat the nucleus material, forming liquid-walled capsule precursor droplets. The solution is cooled with continued agitation, solidifying the waxy walls and forming self-sustaining capsules.

The process described in the foregoing Herbig patent has a number of drawbacks, however, including an undesirably long time span from the formation of liquid droplets to the completely solid capsules (which may cause loss of the active component either via diffusion or exclusion mechanisms into the hot inert oily vehicle); it requires high mechanical agitation; may produce capsules having an uneven distribution of active ingredient; and may produce capsules having a very broad size distribution.

U.S. Pat. Nos. 4,597,970 and 4,828,857, both to Sharma et al., describe a method to encapsulate aspartame in hydrogenated palm oil using a spray drying process. That process has disadvantages shared with other air spray processes, however, in that it is difficult to provide a uniform, continuous layer on the outermost surface of the droplets during the congealing step.

U.S. Pat. No. 3,423,489, to Arens et al. and U.S. Pat. No. 3,779,942 to Bolles describe methods of forming capsules by forming concentric biliquid columns having an inner core of liquid to be encapsulated and an outer tube of hardenable liquid encapsulating material. A special multiple orifice liquid discharging system is used to eject the column along a trajectory path through, e.g., a gaseous phase, for a time sufficient to allow the column to constrict into individual droplets, so that the encapsulating material encloses the encapsulated liquid.

Torchilin et al, "Liposome-Polymer Systems. Introduction of Liposomes into a Polymer Gel and Preparation of the Polymer Gel inside a Liposome", in *Polymer. Sci. U.S.S.R.*, 30:2307-2312 (1988), describes studies on the entrapment of liposomal particles in non-absorbable hydrogels. Liposomes may be difficult to prepare and stabilize. Also, the non-absorbable nature of polyacrylamide hydrogels precludes implantation without subsequent retrieval. As reported by Bailey et al., "Synthesis of Polymerized Vesicles with Hydrolyzable Linkages", *Macromolecules*, 25:3-11 (1992), while synthesis of polymerizable liposome vesicles also has been attempted, the complicated synthesis scheme makes entrapment of drug molecules difficult in this process.

U.S. Pat. No. 5,618,563 to Berde et al. describes use of a polymeric matrix, including microspheres, to release analgesic agents locally at the site of implantation. The polymer matrix used in that patent is not a hydrogel, and hydrophobic polymers are used for entrapment of the drugs. Such polymer matrices, however, may be inflammatory.

U.S. Pat. No. 4,530,840 to Tice et al. describes a method for forming microcapsules to deliver an anti-inflammatory agent. The microcapsules are prepared by dissolving the anti-inflammatory agent and a biodegradable wall-forming material in a solvent, and then dispersing the resulting solution in a continuous phase processing medium. The processing medium evaporates a portion of the solvent from the dispersion, thereby forming microparticles containing the anti-inflammatory agent. The organic solvents described in this method may damage some sensitive therapeutic entities, and residual solvents used in the process may be difficult to remove and present a toxicity concern.

U.S. Pat. No. 5,650,173 to Ramstack et al. reviews the state of the art of formation of microparticles suitable for encapsulating drugs and for providing controlled drug delivery. One method for preparing biodegradable microparticles is described that uses solvents to dissolve both the wall-forming agent and the drug. An extraction medium is used to remove the solvents and stabilize the resulting emulsion to form the microparticles. As with the methods described in the Tice patent, the use of organic solvents in large amounts may raise removal and toxicity issues.

In view of the foregoing, it would be desirable to provide compositions and methods for implementing a locally implantable and absorbable drug delivery system that is capable of delivering relatively low molecular weight compounds in a sustained fashion within hydrogel-based matrices that are easy to process and fabricate.

b. Targetable Microspheres

Numerous disease states in the body are manifested as local conditions and thus may be addressed by local therapies. In addition, local pain (such as from an incision) or solid tumors may be treated locally. Targeting of local therapy may be assisted by a host of non-invasive and invasive detection techniques such as magnetic resonance imaging, ultrasound, x-rays, angiography, etc.

Despite the availability of such diagnostic tools, however, the pinpointing of the location of a disease may at times be more difficult. This may be so either due to the diffuse nature of the disease or due to subtle alterations at the cellular or microscopic level that escape detection by conventional means, for example metastatic tumors or autoimmune disorders. Potent drugs with known efficacy exist for several such diseases, but too many of these drugs have undesirable toxicity profiles at therapeutic levels.

Efficient utilization of a drug by targeted delivery may enable reduction of concomitant toxicity. For example, microspheres for intravenous injectable drug delivery typically should be of a size so as to not to be rapidly cleared from the blood stream by the macrophages of the reticuloendothelial system. U.S. Pat. No. 5,565,215 to Gref et al. describes formation of injectable nanoparticles or microparticles that have variable release rates or that target specific cells or organs.

Liposomal drug delivery systems have been extensively considered for the intravenous administration of biologically active materials, because they were expected to freely circulate in the blood. It has been observed, however, that liposomes are quickly cleared from the blood by uptake through the reticuloendothelial system. Coating of liposomes with poly(ethylene glycol) has been observed to increase substantially the half life of such active materials. The flexible and relatively hydrophilic PEG chains, however, induce a steric effect at the surface of the liposome that reduces protein adsorption and thus RES uptake. See, e.g., Lasic et al., "Sterically Stabilized Liposomes: a Hypothesis on the Molecular Origin of the Extended Circulation Times", *Biochimica et Biophysica Acta*, 1070:187-192 (1991); and Klibanov et al., "Activity of Amphipathic Poly(ethylene glycol) 5000 to Prolong the Circulation Time of Liposomes Depends on the Liposome Size and Is Unfavorable for Immunoliposome Binding to Target", *Biochimica et Biophysica Acta*, 1062: 142-148 (1991).

The field of immunology has enriched our understanding of cell surface receptors and signaling molecules. For example, most cell populations exhibit a unique set of receptors that makes it possible to create "monoclonal antibodies" that are cell population and target specific. Knowledge of this specificity has enabled the development of therapies such as those adopted by fusion toxins, that bind cytotoxic molecules (such as ricin) to monoclonal antibodies against specific receptors of a certain cell population (such as tumor cells). Such therapies generally have not been widely successful, however, for reasons that are not well understood. For example, there may be inadequate selectivity in targeting due to the brief exposure time afforded by intravascular administration of these soluble molecules prior to rapid clearance.

Approaches toward enhancing circulation time using immunoliposomes have been more successful in assimilation in the target organs of interest. Since liposomes are only a few nanometers in size, however, these materials have a much higher circulation velocity. See, e.g., Ley et al., "Endothelial, Not Hemodynamic, Differences Are Responsible for Preferential Leukocyte Rolling in Rat Mesenteric Venules", *Circ. Res.*, 69:1034-1041 (1991). This rapid circulation may interfere with the building of strong interactions with the target tissues by providing only limited exposure to the liposomes.

The adhesion of leukocytes in general, and monocytes in particular, to vascular endothelium is a crucial first step to the recruitment of cells from the blood to the site of tissue damage. Leukocytes do not simply circulate within blood vessels but rather experience a "rolling" type of motion along the vessel wall that allows them to interact with the endothelial cell lining. This rolling motion is believed to be caused by weak interactions mediated by carbohydrate molecules (called selectins) present on the cell surface.

Upon receiving an appropriate activation signal, the endothelial cells slow down (mediated by L and possibly P selectins), and subsequently form more firm attachments (usually mediated by protein-based receptors such as integrins), as reported in Raud et al., "Leukocyte Rolling and Firm Adhesion in the Microcirculation", *Gastroenterology*, 104:310-323 (1993). This in turn causes a local accumulation of leukocytes and allows their participation in physiological processes such as inflammation and repair. Often this behavior is associated with vascular injuries associated with inflammatory conditions. For example, after cardiac bypass procedures, endothelial cells that become anoxic may change their selectin expression pattern and cause neutrophils to attack, thereby causing potentially life-threatening "reperfusion injury," as reported in Edginton, "New Horizons for Stem-Cell Bioreactors", *Bio/Technology*, 10:1099-1106 (1992).

Much of septic shock is mediated by similar mechanisms. The progression of several diseases, such as arthritis and cancer, may be altered by stopping leukocyte adherence, which is the first step to extravasation (movement into the tissue spaces). Much may be learned from how the body targets specific disease sites through receptor mediated guidance.

Accordingly, it would be desirable to provide compositions and methods that enhance the targetability of microencapsulated drug carriers, which may be readily prepared and administered, but are still highly specific in finding the target tissue and efficient in the delivery of the drug. Such "smart microspheres" may be able to achieve improved targeting by having lower circulation velocity, slower clearance from circulation, and by possessing selective adhesivity to selected cellular targets.

SUMMARY OF THE INVENTION

In view of the foregoing, it is an object of the present invention to provide locally implantable and absorbable drug delivery compositions and methods that are capable of delivering relatively low molecular weight compounds.

It is also an object of the present invention to provide locally implantable and absorbable drug delivery compositions and methods capable of delivering relatively low molecular weight compounds in a sustained fashion using hydrogel-based matrices that are easy to process and fabricate.

It is another object of this invention to provide absorbable drug delivery compositions and methods that enhance the targetability of microencapsulated drug carriers, and which may be readily prepared and administered.

It is a further object of this invention to provide absorbable drug delivery compositions and methods that have lower circulation velocities, slower clearance from circulation, and that possess selective adhesivity to selected cellular targets.

It is yet another object of the present invention to provide drug-laden microspheres that provide improved conjugation with specific bioactive receptors.

These and other objects of the invention are accomplished by providing compositions and methods to control the release of relatively low molecular weight therapeutic species using hydrogels. In accordance with the principles of the present invention, a therapeutic species first is dispersed or dissolved within one or more relatively hydrophobic rate modifying agents to form a mixture. The mixture may be formed into microparticles, which are then entrapped within a bioabsorbable hydrogel matrix so as to release the water soluble therapeutic agents in a controlled fashion. Alternatively, the microparticles may be formed in situ during polymerization of the hydrogel.

In one method of the present invention, hydrogel microspheres are formed from polymerizable macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Pre-formed microparticles containing the water soluble therapeutic agent may be dispersed in the polymerizable phase, or formed in situ, to form an emulsion. Polymerization and crosslinking of the emulsion and the immiscible phase is initiated in a controlled fashion after dispersal of the polymerizable phase into appropriately sized microspheres, thus entrapping the microparticles in the hydrogel microspheres.

In another aspect of the present invention, the hydrogel microspheres are formed having a size that will provide selective deposition of the microspheres, or may linked with ligands that target specific regions or otherwise affect deposition of the microspheres within a patient's body.

BRIEF DESCRIPTION OF THE DRAWING

Further features of the invention, its nature and various advantages will be more apparent from the accompanying drawings and the following detailed description of the preferred embodiments, in which.

DETAILED DESCRIPTION OF THE INVENTION

Figure 1:
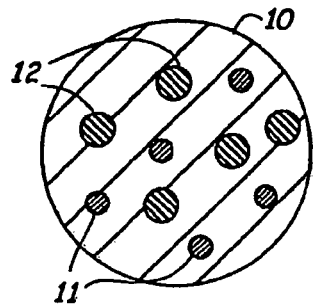
FIG. 1 illustrates a composite hydrogel microsphere formed in accordance with the principles of the present invention containing dispersed drug-containing microdomains.

This written description outlines the compositions and methods of the present invention to from drug delivery systems, describes absorbable polymers and therapeutic agents suitable for use therewith, and methods of forming the composite hydrogel drug delivery systems of the present invention. A variety of agents suitable for controlling the rate of release of therapeutic agents from the hydrogel matrix is described, together with factors and methods for influencing the rate of release of therapeutic agents from the hydrogels. Methods of targeting the hydrogel microspheres for specific applications are set forth. Several examples of hydrogel-based drug delivery systems prepared in accordance with the present invention, are provided.

In overview, the present invention is directed to compositions and methods for forming composite hydrogel-based matrices and microspheres having entrapped therapeutic compounds. Preferably, a bioactive agent is entrapped in microparticles having a hydrophobic nature (herein called "hydrophobic microdomains"), to retard leakage of the entrapped agent. More preferably, the composite materials that have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase).

The oil phase entraps the drug and provides a barrier to release by slow partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent. For water soluble drugs, or drugs that are likely to be denatured by contact with aqueous phases, however, the release rate modifying agent may be selected from a variety of alternatives, described hereinbelow.

Routes of administration of hydrogel-based drug delivery systems prepared in accordance with the present invention include, but are not limited to: inoculation or injection (e.g., intra-peritoneal, intra-muscular, subcutaneous, intra-aural, intra-articular, intra-mammary, etc.), topical application (e.g., on areas, such as eyes, ears, skin or on afflictions such as wounds, burns, etc.), and by absorption through epithelial or mucocutaneous linings (e.g., vaginal and other epithelial linings, gastrointestinal mucosa, etc.). The compositions formulated using hydrogel matrices may include previously known pharmaceutical carriers or excipients, adjuvants, etc.

The hydrogel matrices in accordance with the present invention may be formed into capsules, tablets, films, microspheres and the like. Matrices in the form of discs, slabs or cylinders may be used as implants, while microspheres may be applied as subcutaneous, intramuscular, intravenous or intra-arterial injectables. The term "microsphere" means a piece of hydrogel that is of a size ranging from a few millimeters to a few nanometers in size. It may be spherical, hollow spherical, or irregularly shaped.

The hydrogel matrix preferably includes a biologically-active agent, either singly or in combination, such that the implant precursor and implant provide a delivery system for the agent adjacent to or distant from tissues and organs in the animal. Biologically-active agents, which may be used alone or in combination in the implant precursor and implant, include, for example, a medicament, drug, or other suitable biologically-, physiologically-, or pharmaceutically-active substance that is capable of providing local or systemic biological, physiological or therapeutic effect in the body of an animal, including a mammal, and of being released from the solid implant matrix into adjacent or surrounding tissue fluids.

The biologically-active agent may be soluble in the polymer solution to form a homogeneous mixture, or insoluble in the polymer solution to form a suspension or dispersion. Upon implantation, the biologically-active agent preferably becomes incorporated into the implant matrix. As the matrix degrades over time, the biologically-active agent is released from the matrix into the adjacent tissue fluids, preferably at a controlled rate. The release of the biologically-active agent from the matrix may be varied, for example, by the solubility of the biologically-active agent in an aqueous medium, the distribution of the agent within the matrix, the size, shape, porosity, solubility and biodegradability of the implant matrix, and the like.

The biologically-active agent may stimulate biological or physiological activity within the animal. For example, the agent may act to enhance cell growth and tissue regeneration, function in birth control, cause nerve stimulation or bone growth, and the like. Examples of useful biologically-active agents include a substance, or metabolic precursor thereof, that is capable of promoting growth and survival of cells and tissues, or augmenting the functioning of cells, as for example, a nerve growth promoting substance such as a ganglioside, a nerve growth factor and the like; a hard or soft tissue growth promoting agent such as fibronectin (FN), human growth hormone (HGH), protein growth factor interleukin-1 (IL-1) and the like; a bone growth promoting substance such as hydroxyapatite, tricalcium phosphate and the like; and a substance useful in preventing infection at the implant site, for example, an antiviral agent such as vidarabine or acyclovir, an antibacterial agent such as a penicillin or tetracycline, or an antiparasitic agent such as quinacrine or chloroquine.

While substantial utility of this invention lies in the encapsulation and controlled release of substantially water soluble drugs, other therapeutic entities having very limited water solubility may be readily incorporated and delivered using the drug delivery matrices of this invention.

Suitable Absorbable Hydrogels

The hydrophilic phase of the drug delivery system of the present invention (i.e., the matrix or continuous phase that is permeable to moisture) may consist of any of the biodegradable hydrogel-type materials described hereinabove. For illustration purposes, an aqueous solution of a water soluble and polymerizable macromer that may be polymerized to form a bioabsorbable hydrogel is described in the Examples set forth hereinbelow. The synthesis, characterization, and the formation of such hydrogels is described, e.g., in Sawhney et al., "Bioerodible Hydrogels Based on Photopolymerized Poly (ethyleneglycol)-co-poly (α-hydroxy acid) Diacrylate Macromers", *Macromolecules,* 26:581-587 (1993)

Therapeutic Molecules

Several previously known and recently discovered therapeutic entities have relatively low molecular weights (defined as a molecular weight less than 100,000 daltons) and are relatively water soluble (having a solubility of more than 0.001 mg/mL). Hydrogel matrices typically are swollen with water, thus any dissolved or dispersed therapeutic entity also has free access to the aqueous surroundings. The dispersal of such entities within a hydrogel matrix is known to produce a rapid release of the therapeutic entity, e.g., release is substantially complete within a few days at the most.

It is often desirable, however, to extend the release of such therapeutic agents to several days, weeks, or even months. Also, it is desirable to have a release rate that is controlled and gradual over this time period, with zero order kinetics or time independent release being most preferred and desirable.

Therapeutic entities having molecular weights less than 100,000 daltons, more preferably less than 20,000 daltons, and most preferably less than 2,000 daltons, and that have a water solubility of more than 0.001 mg/mL, more preferably more than 0.01 mg/mL, and most preferably more than 0.1 mg/mL, advantageously may be used in drug delivery systems of the present invention. These therapeutic agents include, for example, physiologically active materials or medicinal drugs (such as agents affecting the central nervous system, antiallergic agents, cardiovascular agents, agents affecting respiratory organs, agents affecting digestive organs, hormone preparations, agents affecting metabolism, antitumor agents, antibiotic preparations, chemotherapeutics, antimicrobials, local anesthetics, antihistaminics, antiphlogistics, astringents, vitamins, antifungal agents, peripheral nervous anesthetics, vasodilators, crude drug essences, tinctures, crude drug powders, hypotensive agents, or immunosuppressants).

Several oligopeptide drugs, including cytokines and growth factors, also may be used as therapeutic agents. The terms "cytokine" and "growth factor" are used to describe biologically active molecules and peptides (which may be either naturally occurring or synthetic) that aid in healing or regrowth of normal tissue. The function of cytokines is twofold: (1) to incite local cells to produce new collagen or tissue, and (2) to attract cells to the site in need of correction. As such, cytokines and growth factors serve to encourage "biological anchoring" of an implant within host tissue.

The cytokines either may be admixed with a conjugate or chemically coupled to a conjugate. For example, cytokines suitable for use in the drug delivery systems of the present invention include interferons (IFNs), tumor necrosis factors (TNFs), interleukins, colony stimulating factors (CSFs), growth factors such as osteogenic factor extract (OFE), epidermal growth factor (EGF), transforming growth factor (TGF) alpha, TGF-β (including any combination of TGF-βs), TGF-β1, TGF-β2, platelet derived growth factor (PDGF-AA, PDGF-AB, PDGF-BB), acidic fibroblast growth factor (FGF), basic FGF, connective tissue activating peptides (CTAP), β-thromboglobulin, insulin-like growth factors, erythropoietin (EPO), nerve growth factor (NGF), bone morphogenic protein (BMP), osteogenic factors, and the like.

The drug delivery systems of the present invention may be designed to release appropriate encapsulated or unencapsulated growth factors, including epidermal growth factors, human platelet derived TGF-β, endothelial cell growth factors, thymocytic-activating factors, platelet derived growth factors, fibroblast growth factor, fibronectin or laminin.

Suitable biologically-active agents for use in the invention also include anti-inflammatory agents such as hydrocortisone, prednisone and the like; antibacterial agents such as penicillin, cephalosporins, bacitracin and the like; antiparasitic agents such as quinacrine, chloroquine and the like; antifungal agents such as nystatin, gentamicin and the like; antiviral agents such as acyclovir, ribavirin, interferons and the like; antineoplastic agents such as methotrexate, 5-fluorouracil, adriamycin, tumor-specific antibodies conjugated to toxins, tumor necrosis factor and the like; analgesic agents such as salicylic acid, acetaminophen, ibuprofen, flurbiprofen, morphine and the like; local anesthetics such as lidocaine, bupivacaine, benzocaine and the like; vaccines such as hepatitis, influenza, measles, rubella, tetanus, polio, rabies and the like; central nervous system agents such as a tranquilizer, β-adrenergic blocking agent, dopamine and the like; human growth hormone, insulin-like growth factor and the like; hormones such as progesterone, follicle stimulating hormone, insulin, somatotropins and the like; antihistamines such as diphenhydramine, chlorphencramine and the like; cardiovascular agents such as digitalis, nitroglycerine, papaverine, streptokinase and the like; vasodilators such as theophylline, niacin, minoxidil and the like; and other like substances.

The drug delivery systems of the present invention may also be used to provide controlled antibiotic delivery, including such antibiotics as aminoglycosides, macrolides such as erythromycin, penicillins, cephalosporins and the like; anesthetic/analgesic delivery pre- or post-surgery or to treat pain using such agents as amide-type local anesthetics like lidocaine, mepivacaine, pyrrocaine, bupivacaine, prilocaine, etidocaine and the like; and local controlled delivery of non-steroidal anti-inflammatory drugs such as ketorolac, naproxen, diclofenac sodium and flurbiprofen. It is recognized that in certain forms of therapy, combinations of agents/drugs in the same delivery system (i.e., polymer of the invention) may be useful to obtain an optimal effect. Thus, for example, an antibacterial and an anti-inflammatory agent may be combined in a single polymer to provide combined effectiveness.

It is intended that the water soluble drugs discussed hereinabove be illustrative, not limiting. Examples of other water soluble agents include peptides having biological activities, antipyretics, analgesics, anti-inflammatory agents, antitussive expectorants, sedatives, muscle relaxants, antiepileptic agents, antiulcer agents, antidepressants, antiallergic agents, cardiotonics, antiarrhythmic agents, antidiabetic agents, anticoagulants, hemostatics, antituberculous agents, narcotic antagonists, bone resorption inhibitors and angiogenesis inhibitors.

Particular water soluble polypeptides which may be used in this invention include, for example, oxytocin, vasopressin, adrenocorticotrophic hormone (ACTH), transforming growth factor antagonists, prolactin, luliberin or luteinizing hormone releasing hormone (LH-RH), LH-RH agonists or antagonists, growth hormone, growth hormone releasing factor, insulin, somatostatin, bombesin antagonists, glucagon, interferon, gastrin, tetragastrin, pentagastrin, urogastrone, secretin, calcitonin, enkephalins, endomorphins, angiotensins, renin, bradykinin, bacitracins, polymyzins, colistins, tyrocidin, gramicidines, monoclonal antibodies, soluble vaccines, and synthetic analogues, modifications and pharmaceutically-active fragments thereof.

Examples of antitumor agents that may be suitable for delivery using the delivery systems of the present invention include bleomycin hydrochloride, methotrexate, actinomycin D, mitomycin C, vinblastine sulfate, vincristine sulfate, daunorubicin hydrochloride, adriamycin, neocarzinostatin, cytosine arabinoside, fluorouracil, tetrahydrofuryl-5-fluorouracil krestin, picibanil, lentinan, levamisole, bestatin, azimexon, glycyrrhizin, poly I:C, poly A:U, poly ICLC, Cisplatin and the like.

A variety of radiotherapeutic compounds such as gamma or beta radiation emitting species also may be included within the drug delivery systems of the current invention. The presence of therapeutic radiation may be used to control the proliferation of undesirable cells, such as occur during cancer or during hyperplasia. Hyperplastic response from injured organs such as arteries are widely believed to be responsible for restenosis following angioplasty. Isotopes of iodine, phosphorus, palladium etc. therefore may be suitable for this purpose.

Other previously known beneficial drugs are described in *Pharmaceutical Sciences*, by Remington, 14th Ed., 1979, published by Mack Publishing Co.; *The Drug, The Nurse, The Patient, Including Current Drug Handbook*, by Falconer et al., 1976, published by Saunder Company; and *Medicinal Chemistry*, 3rd Ed., Vol. 1 and 2, by Burger, published by Wiley-Interscience Co.

Formation of Hydrophobic Domains

Hydrophobic microdomains, by themselves, may be degraded or quickly cleared when administered in vivo, making it difficult to achieve prolonged release directly using microdroplets or microparticles containing the entrapped agent in vivo. In accordance with the present invention, however, the hydrophobic microdomains are sequestered in a gel matrix. The gel matrix protects the hydrophobic microdomains from rapid clearance, but does not impair the ability of the microdroplets or microparticles to release their contents slowly.

Referring to FIG. 1, an illustrative multiphase hydrogel microsphere, or portion of a hydrogel matrix, constructed in accordance with the present invention is described. Microsphere 10 comprises a continuous hydrogel matrix in the form of a sphere, droplet, other irregular particulate shape, or portion of a gel matrix, containing microparticles 11 and/or microdroplets 12 dispersed throughout its volume. Microparticles 11 may be preformed, and mixed with a polymerizable phase prior to polymerization to form the hydrogel microsphere. Microdroplets 12, on the other hand, may be formed in situ by entrapment of a therapeutic agent-laden hydrophobic phase during emulsion polymerization of microsphere 10. Microspheres 10 may be dried to enhance shelf stability.

Microdroplets 12 also may comprise molecular compounds that are not water soluble, compounds with limited water solubility, or compounds with limited water solubility in solution in another phase that is immiscible with the hydrogel phase. Molecular compounds that are not stable in an aqueous solution also may be contained within a phase having very limited water permeation and partitioning.

In one embodiment, a microemulsion of a hydrophobic phase and an aqueous solution of a water soluble molecular compound, such as a protein, peptide or other water soluble chemical is prepared. The emulsion is of the "water-in-oil" type (with oil as the continuous phase) as opposed to an "oil-in-water" system (where water is the continuous phase). As used herein, the term "continuous phase" refers to the external hydrogel phase, as compared to the "dispersed phase", which is the internal phase.

The water or dispersed phase comprises a dispersion of a water soluble drug in a microparticulate fashion. The "external" oil phase of the microsphere includes a release rate modifying agent, which typically is incompatible with the solvent, e.g., water or an aqueous buffer, of the hydrogel-forming preparation. Because the molecular compound is effectively "trapped" within multiple tiny oil droplet reservoirs formed throughout the hydrogel matrix, the incorporated molecular compound does not partition readily into the outer hydrophilic gel or solution phase during formulation.

The hydrophobic oil phase may be formed by one of several methods, including spray-forming and oil-based hot melt microencapsulation. In the spray-forming method, a low melting temperature release rate modifying agent is used and a known amount of the active drug is suspended (for insoluble drugs) or co-dissolved (for soluble drugs) by a melt mixing step. The solution or dispersion is then sprayed into a cooled stream of air, a bath of cold water, or a hydrogel precursor solution. Microparticles ranging in size between 1-10 microns are obtained, having a morphology that depends on the type of release rate modifying agent used and its melt viscosity.

In an oil-based hot melt microencapsulation method, the release rate modifying agent is first melted and then mixed with solid particles of drug that have been sieved to less than 50 microns. The mixture is suspended in a non-miscible solvent (like silicon oil), and, with continuous stirring, heated to 5° C. above the melting point of the release rate modifying agent. Once the emulsion is stabilized, it is cooled until the particles solidify. The resulting microparticles are washed by decantation with petroleum ether to give a free-flowing powder. Microparticles with sizes between 1 to 1000 microns can thus be obtained.

Alternatively, the oil phase microdroplets also may be formed in situ by heating the polymerizable solution. Once the desired drug-containing hydrophobic domains are obtained, they may be dispersed in a continuous polymerizable aqueous solution phase to form an emulsion. The emulsion is then polymerized to entrap and stabilize the hydrophobic microdomains. Oil soluble drugs may be dissolved in the hydrophobic phase while water soluble drugs may be micronized into this phase to form a fine dispersion. FIG. 1 illustrates a composite hydrogel prepared using the foregoing method.

Proteins and growth factors, which may be denatured by contact with water from the hydrogel environment, first may be lyophilized after micronization and then suspended within an oil phase to form a dispersion. The dispersion then may be emulsified within a macromer solution to form an oil-in-water emulsion that can then be crosslinked to form hydrogel shaped objects or microspheres. The protein, polypeptide or growth factor is expected to remain relatively stable within the oil microenvironment and only slowly diffuse out to the hydrogel environment, from where it is released.

The presence of the oil droplets therefore create a microenvironment for the protein or polypeptide that not only stabilizes the molecules but also controls their release rate. Any of a variety of pharmacologically acceptable oils may be used for this purpose, including but not limited to peanut oil, castor oil, coconut oil, corn oil etc.

Any of a variety of agents that have a limited solubility in both the bulk and the dispersed phase may be used as phase transfer agents and are well known in the art of emulsion polymerization, including surfactants such as the TWEEN® and SPAN® series of surfactants (TWEEN® and SPAN® are registered trademark of ICI Americas, Inc., Wilmington, Del.) and the PLURONIC® series of polyoxyalkylene ethers (PLURONIC® is a registered trademark of BASF Corporation, Mount Olive, N.J.), etc. Organic solvents having solubility in both organic and aqueous phases also may be used and are preferred.

Because formation of the microspheres in accordance with the principles of this invention typically involves an aqueous solution or dispersion, water-miscible organic materials may be used as the phase transfer agents, including but not limited to solvents such as dialkyl sulfoxides, such as dimethyl sulfoxide (DMSO); dialkyl formamides, such as dimethyl formamide (DMF); $C_{1-5}$ alcohols, such as methanol and ethanol; ketones such as acetone and methyl ethyl ketone; and ethers such as tetrahydrofuran (THF), dibutyl ether and diethyl ether.

Suitable water soluble preservatives which may be employed in the drug delivery systems of the present invention include sodium bisulfite, sodium thiosulfate, ascorbate, benzalkonium chloride, chlorobutanol, thimerosal, phenylmercuric borate, parabens, benzylalcohol and phenylethanol. These agents may be present in amounts of from 0.001 to 5% by weight and preferably 0.01 to 2%.

Suitable water soluble buffering agents are alkali or alkali earth carbonates, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4 to 8. The buffering agent therefore may be as much as 5% by weight of the total composition.

Release Rate Modification Agents

Release rate modifying agents that are hydrophobic and able to form a relatively stable dispersed phase within the continuous hydrogel matrix phase may be advantageously used as a secondary container for the substantially water soluble therapeutic entity. The release rate modifying agent retards diffusion of the water soluble therapeutic entity by any of a variety of mechanisms which are not well understood.

For example, the release rate modifying agent may render the therapeutic agent insoluble and in a particulate form, or the crystallinity of the release rate modifying agent may prevent the diffusion of water and thus increase the resistance to release of the therapeutic agent. No particular mechanism for modification of the release rate is postulated and this invention should not be construed to be limited by any one or more such mechanisms.

Any of a variety of low melting fatty acids, fats, oils, waxes, or other relatively hydrophobic species having a melting point preferably below 85° C., more preferably below 65° C., and most preferably below 50 DC, may be used as release rate modifying agents. The release rate modifying agents may be solids or liquids at room temperature. They preferably are selected from species that have a relatively low solubility in water. "Relatively low solubility" means that microparticles made from these substances should take several hours to days, and preferably longer, to fully dissolve in water (if in fact they do fully dissolve at all).

The release rate modifying agents should, however, be pharmaceutically acceptable entities that ultimately are either metabolized or cleared from the physiological environment. Useful release rate modification agents that are dissolved or dispersed within the hydrogel material also may be included, for example organic substances that are relatively water-insoluble (i.e., water immiscible), with water-insoluble substances preferred. It is preferred that a release rate modification agent be compatible with the combination of polymers and solvent used to formulate the polymer solution. A partial list of compounds that suitable for use as release rate modifying agents is set forth in Table 1.

TABLE 1

| Chemical | Melting Point (° C.) |
| --- | --- |
| capric acid | 31.4 |
| undecanoic | 28.5 |
| lauric acid | 44 |
| heneicosanoic (uneicosane) | 74-75 |
| behenic acid | 80 |
| behenic acid, ethyl ester | 50 |
| behenic acid, methyl ester | 54 |
| tricosanoic acid, methyl ester | 55.6 |
| tridecanoic acid | 41-42 |
| pentadecanoic acid | 51-53 |
| heptadecanoic acid | 59-61 |
| heptadecanoic, ethyl ester | 28 |
| heptadecanoic, methyl ester | 31-32 |
| nonadecanoic acid | 68-70 |
| myristic acid | 58 |
| myristic, benzyl ester | 20.5 |
| myristic, methyl ester | 19 |
| palmitic acid | 63 |
| palmitic, benzyl ester | 36 |
| palmitic, butyl ester | 16.9 |
| palmitic, hexadecyl | 53-54 |
| palmitic, methyl ester | 30 |
| palmitic, myricyl ester | 72 |
| palmitic, propyl | 20.4 |
| stearic acid | 71.2 |
| stearic acid, benzyl ester | 28 |
| stearic acid, butyl ester | 27.5 |

TABLE 1-continued

| Chemical | Melting Point (° C.) |
|---|---|
| stearic acid, isobutyl ester | (i) 22.5 |
|  | (ii) 28.9 |
| stearic acid, cyclohexyl ester | 44 |
| stearic acid, ethyl ester | 31-33 |
| stearic acid, hexadecyl ester | 57 |
| stearic acid, methyl ester | 39.1 |
| stearic acid, 3-oxo, ethyl ester | 37-38 |
| stearic acid, 2-hydroxyethyl ester | 60-61 |
| stearic acid, 6-oxo, ethyl ester | 47 |
| stearic acid, 10-oxo, ethyl ester | 41 |
| stearic acid, 12-oxy, ethyl ester | 38 |
| stearic acid, pentyl ester | 30 |
| stearic acid, isopentyl ester | 25.5 |
| stearic acid, phenyl ester | 51-53 |
| stearic acid, isopropyl ester | 28 |
| stearic acid, tetrahydrofufuryl ester | 22 |

Useful release rate modifying agents include, for example, fatty acids, triglycerides, and other like hydrophobic compounds, and may include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl) sebecate, and the like; polyhydroxy alcohols, such as propylene glycol and its oligomers; esters of polyethylene glycol; glycerin; sorbitol; triesters of glycerol, such as triglycerides; epoxidized or oligomerized soybean oil, and other vegetable oils; sterols, such as cholesterol; and alcohols, such as $C_6$-$C_{12}$ alkanols, 2-ethoxyethanol, and the like.

A release rate modifying agent may be used singly or in combination with other such agents. Release rate modifying agents may also be selected from triglyceryl esters such as glyceryl distearate, glyceryl tristearate, glyceryl monostearate, glyceryl dipalmitate, glyceryl tripalmitate, glyceryl monolaurate, glyceryl didocosanoate, glyceryl tridocosanoate, glyceryl monodocosanoate glyceryl monocaprate, glyceryl dicaprate, glyceryl tricaprate, glyceral monomyristate, glyceryl dimyristate, glyceryl trimyristate, glyceryl monodecenoate, glyceryl didecenoate and glyceryl tridecenoate.

Release rate modifying agents also may include waxy compositions selected from the group consisting essentially of beeswax, cetyl palmitate, spermacetic wax, carnauba wax, cetyl myristate, cetyl, palmitate, ceryl cerotate, stearyl palmitate, stearyl myristate and lauryl laurate; natural waxes including vegetable waxes such as carnauba, cauassu, candelilla, raffia, palm esparto, sugar cane and cotton waxes; animal waxes such as beeswax, ghedda, chinese insect, shellac, spermaceti and lanolin waxes; and mineral waxes such as paraffin, microcrystalline, ozokerite, montan and syncera waxes.

Synthetic and modified waxes useful as solid matrix-forming materials, such as chlorinated paraffin wax. It will be appreciated that waxes are a mixture of various components, and that each type of wax is itself available in a number of different grades. Other hydrophobic materials which may be suitable for use as release rate modifying agents in the carrier system are selected from the group consisting of long chain carboxylic acids, long chain carboxylic acid esters, long chain carboxylic acid alcohols and mixtures thereof.

Long chain carboxylic acids useful in forming release rate modifying agents generally will contain from 6-30 carbon atoms, preferably at least 12 carbon atoms, and most preferably 12 to 22. This carbon chain may be fully saturated and unbranched, it may contain one or more double bonds, and it may contain 3-carbon rings or hydroxyl groups. Examples of suitable saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocarboxylic acids. Examples of these are linoleic acid, linolenic acid, arachidonic acid and behenolic acid. Branched acids are useful, including, for example, diacetyl tartaric acid.

Examples of useful long chain carboxylic acid esters include, but are not limited to, those from the group of: glyceryl monostearates; glyceryl monopalmitates; mixtures of glyceryl monostearate and glyceryl monopalmitate (Myvaplex 600, available from Eastman Fine Chemical Company, Rochester, N.Y.); glyceryl monolinoleate; glyceryl monooleate; mixtures of glyceryl monopalmitate, glyceryl monostearate, glyceryl monooleate and glyceryl monolinoleate (Myverol 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (Mverol 18-99, Eastman Fine Chemical Company); acetylated glycerides such as distilled acetylated monoglycerides (Myvacet 5-07, 7-07 and 9-45, Eastman Fine Chemical Company); mixtures of propylene glycol monoesters, distilled monoglycerides, sodium stearoyl lactylate and silicon dioxide (Myvatex TL, Eastman Fine Chemical Company); mixtures of propylene glycol monoesters distilled monoglycerides, sodium stearoyl lactylate and silicon dioxide (Myvatex TL, Eastman Fine Chemical Company); d-alpha tocopherol polyethylene glycol 1000 succinate (Vitamin E TPGS, Eastman Fine Chemical Company); mixtures of mono- and di-glyceride esters; calcium stearoyl lactylate; ethoxylated mono- and di-glycerides; lactated mono- and diglycerides; lactylate carboxylic acid esters of glycerol and propylene glycol; lactylic esters of long chain carboxylic acids; polyglycerol esters of long chain carboxylic acids; propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_{10}$-$C_{30}$ cholesterol/lavosterol esters; and sucrose long chain carboxylic acid esters.

Alcohols useful in the invention are exemplified by the hydroxyl forms of the carboxylic acids listed above and also cetearyl alcohol.

Factors Affecting Release Rates

The diffusion of a hydrophobic drug, dissolved in a hydrophobic phase where it has good solubility, into hydrophilic surroundings, is slow. The rate of drug diffusion from hydrophobic domains is expected to be a function of domain size, dispersed phase fraction, and the relative solubility or the partition coefficient of the drug across the two phases. As the microdomains are either liquid or solidified from low melting point solids without the use of any solvents that can cause defects or "channels" during evaporation, phase inversion, or sublimation, they are expected to be free of defects causing problems such as large burst effects.

Once the drug is released into the continuous hydrogel phase, diffusion and release is expected to be rapid since these hydrogels are known not to provide a significant resistance to diffusion of small molecules. Hydrophilic small molecules that are dispersed in the oil phase are expected to have limited solubility in the hydrophobic phase and are expected to dissolve very slowly as the drug is transported into the hydrogel phase. Thus, it is expected that a saturated level of hydrophilic drug may be maintained within the hydrophobic domains, thereby resulting in substantially "zero order" or constant release from such composite devices.

Changes in hydrophilicity and lipophilicity of the hydrogel matrix material compared to the release rate modifying agent are expected to have a substantial effect on the release rate of the drug being delivered. Other factors, such as dispersion size, distribution, relative drug loading and composition of each of the two phases, are also expected to affect release rates.

The gel matrix may be a second rate-limiting factor in the release of the bioactive agent. In general, for low molecular weight bioactive agents (e.g., agents approximately 2,000 daltons or less in molecular weight) the porosity of the gel matrix is not expected to be relevant to the rate of release of the bioactive agent, because in most cases such agents will freely diffuse through any gel. For example, most antibiotic compounds are expected to diffuse freely through gel matrices of the present invention, and the composition of the membrane formed by the release rate modifying agent will govern the rate of release of entrapped agent.

On the other hand, the pore size of the gel may become a rate limiting factor in diffusion of a bioactive agent that is released from sequestered liposomes where the bioactive agent is of relatively large molecular weight. Generally, hydrogels exclude molecules of $10^5$ daltons or larger in molecular weight. The pore size of hydrogels depends upon the concentration of the starting macromer or monomer used to make the gel (generally 4 to 30% w/w concentrations of the precursors are used to prepare gels). The pore size may be varied further by the degree of crosslinking and the molecular weight between crosslinks of the gel. For example, if the molecular weight of the bioactive agent is known, one skilled in the art could prepare a gel to obtain the approximate diffusion rate desired by controlling crosslinking of the gel, hence controlling its pore size.

In addition to parameters such as the size of the bioactive agent and porosity of the gel (which may be used to control the rate of diffusion of bioactive agents released from sequestered liposomes), the nature of the bioactive agent and the gel will themselves further affect the rate of diffusion. Thus, if the bioactive agent has any affinity for the gel matrix (e.g., affinity based upon charge, hydrogen bonding, van der Waals forces, etc.), diffusion through the gel of the bioactive agent released from the sequestered liposomes will be slowed.

In addition, irrespective of the gel matrix that is used, the gel matrix will be freely permeable to fluids to which it is exposed, e.g., to tissue or body fluids or culture media, except for molecules that have molecular weights higher than the permeability limit of the gel. Thus, microparticles within the gel matrix will interact only with molecules that are able to diffuse through the gel matrix.

The hydrogel matrix also may be used to modify the release of the therapeutic compound by limiting its diffusion by means other than the pore size effect. For example, U.S. Pat. No. 5,693,341 to Schroeder et al., which is incorporated herein by reference, describes affinity-bound collagen matrices for the delivery of biologically active agents. Those collagen matrices are formed by mixing a binding ligand and an active agent together, allowing the resulting binding ligand-active agent mixture to form an affinity-bound complex, and then combining the resulting affinity-bound complex with collagen to form a matrix.

The foregoing method of using binding ligands also may be used in the hydrogel drug delivery devices of the present invention by including the binding ligands as part of the hydrogel matrix, while the active agent is present either within the matrix itself or in the secondary containment of a hydrophobic microdomain. Thus, the release of the active agent may be inhibited and controlled by the presence of an affinity ligand within the hydrogel matrix.

The preferred binding ligand, heparin, has been shown to form affinity-bound complexes with a number of active agents, including without limitation: antithrombin III Factors VII, IX, XI, XII, and XIIa; thrombin; properdin; complements C1, C2, C3 and C4; complement factor β, C3b inactivator; Gc globulin; protein HC; fibronectin; β2-glycoprotein 1; C-reactive protein; lipoprotein lipase; hepatic triglyceride lipase; VLDL, LDL; VLDL apoprotein; HDLP; restriction endonucleases; RNA polymerase; RNA polymerases I and II; DNA polymerase; DNA ligase; polynucleotide kinase; elongation factor (EF-1); initiation factors; protein synthesis factors; ribosomes; estrogen receptor; androgen receptor; platelet factor 4; SV 40 tumor antigen; Hepatitis B surface antigen; hyaluronidase; collagenase inhibitor; neurophysin; and trehalose phosphate synthetase.

Heparin is also known to form affinity-bound complexes with the following agents: transforming growth factor beta (TGF-β), fibroblast growth factor (FGF), platelet-derived growth factor (PDGF), epidermal growth factor (EGF), osteogenin, insulin-like growth factors (IGFs), vascular endothelial growth factor, granulocyte/macrophage colony-stimulating factor (CSF), gamma interferon, glia-activating factors, and collagen type V.

A permeation model that allows estimation of hydrogel porosity and tortuosity, and thus allows for the computation of an effective diffusivity of a solute within a hydrogel, is reported in Dong, et al., *J. Biomater. Sci. Polymer Edn.*, 5:473-484 (1994). The release rates of various drugs from hydrogel matrices may be determined if all necessary parameters and physical properties of the drug to be released, the release rate modifying agent, and the hydrogel matrix material, are known.

Targetable Microspheres

The size of the hydrogel bodies may be selected so as to direct their ultimate placement. Thus, depending on size, intravenously introduced microspheres may be physically trapped in the capillary beds of the lungs (sizes greater than 7 μm), phagocytosed by cells of the RES system (sizes greater than 100 nm), causing the particles to accumulate mainly in the liver and spleen, or may become lodged at extracellular sites (sizes less than 100 nm).

Hydrogel microspheres may be formed that mimic attributes of circulating blood cells, such as their size, distribution, circulation and clearance, and density, among others. Microspheres that meet these characteristics further may be modified to improve their targeting by coupling pendant tethers, attached to the microsphere at one end and with specific signaling molecules at the other.

More generally, the microcapsules of the present invention optionally may be linked with ligands that minimize tissue adhesion or that target the microcapsules to specific regions, thereby enabling specific therapeutic agents to be delivered to organs of interest. For example, the liver may be targeted by forming hydrogel microspheres containing a therapeutic agent entrapped in a release rate modifying agent so that the microsphere expresses the asialoglycoprotein receptor on its surface and thus can be used to specifically target the liver through the vascular system.

Such microspheres may have the ability to bind to target cells, but are not expected to extravasate, thus providing sustained protection and masking of potential targets from leukocytes.

Microspheres prepared in accordance with the present invention also potentially may act as therapeutic entities by competing for selectin mediated attachment, thereby interfering with leukocyte binding. In addition, they also may be able to target the delivery of antiinflammatory, antibiotic, antioxidant, or antitumor compounds more specifically to sites of disease.

EXAMPLES

Example 1

Formation of Hydrogel Microspheres

Almost monodisperse hydrogel microspheres, similar in size and density to circulating white blood cells such as neutrophils and leukocytes, may be formed that contain dangling functional groups or a bio-active agent. One way of forming such microspheres is by creating a water in oil suspension using an aqueous solution of a water soluble free radical polymerizable macromer.

Preparation of Microdroplets in Accordance with the Present Invention on a laboratory scale is possible using sonication induced by a probe sonicator. For industrial scale production, Microfluidization® (Microfluidics Corp., Newton, Mass.) is preferred. That process creates high shear by colliding opposing jets of liquid. The apparatus is described by Mayhew et al., "Characterization of Liposomes Prepared Using a Microemulsifier", *Biochim. Biophys. Acta*, 775:169-174 (1984). Alternative industrially scalable processors include, but are not limited to, the Gaulin and Rannie Homogenizers (APV Gaulin/Rannie Homogenizers, St. Paul, Minn.).

Synthesis and characterization of water soluble macromers that can be polymerized to form biodegradable hydrogels are reported in Sawhney et al., "Bioerodible Hydrogels Based on Photopolymerized Poly(ethyleneglycol)-co-poly(α-hydroxy acid) Diacrylate Macromers", *Macromolecules*, 26:581-587 (1993).

Figure 2:
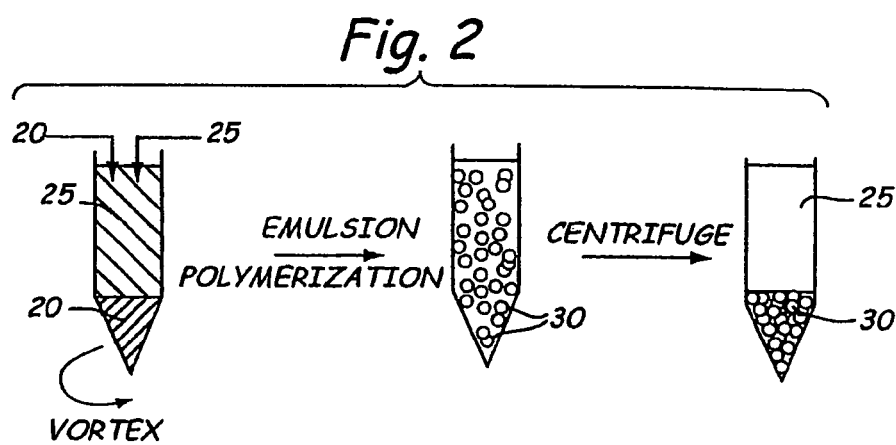
FIG. 2 illustrates steps in forming the hydrogel microspheres of the present invention using an emulsion polymerization method.

Referring now to FIG. 2, the steps of fabricating hydrogel microspheres in accordance with the methods of the present invention are described. First, aqueous phase 20 containing a metallic salt (such as ferrous gluconate at a concentration of 50 to 50,000 ppm) is added to oil phase 25, comprising an oil soluble peroxide or hydroperoxide (at a concentration of 10 to 100,000 ppm) to initiate a redox reaction. This reaction may be initiated after a monodisperse population of microdroplets has been obtained by an appropriate shearing mechanism. For example, the reaction may be controlled by first dispersing aqueous phase microdroplets within the oil phase until the required size distribution has been attained. Stirring may be continued and a further amount of oil phase, carrying the peroxide dissolved in it, is then introduced and mixed in. The aqueous phase microdroplets may contain any of the low molecular weight water soluble therapeutic compounds described hereinabove.

The resulting microdroplets of macromer polymerize to form hydrogel microspheres 30. Peroxides that are soluble in the oil phase or the water soluble peroxides can be dissolved in a phase transfer agent, that then carries the water soluble peroxide into the oil phase and also facilitates the transport of the peroxide into the hydrogel microdroplet. This phase transfer effectively initiates polymerization in the presence of the reducing agent, which is already present in the macromer solution.

The droplet size will depend on oil and water phase viscosities, their relative surface energies, the presence of stabilizers and surfactants, and the shearing mechanism. Any of a variety of oils of natural or synthetic origin can be used. The microspheres then may be isolated by centrifugation and may be washed free of the oil phase by rinsing with aqueous solutions. The resulting hydrogel microspheres may be used shortly after preparation, or may be stored frozen, dried, or lyophilized until such time as use is expected, in order to provide a shelf-stable drug delivery matrix.

It is not necessary to use the redox-type initiation to form such microspheres and any of a variety of chemical, thermal, or photochemical free radical initiating systems, such as are previously known in the art, may be used. It is not essential that free radically-polymerizable macromers be used at all. For example, any of a variety of nucleophilic or electrophilic reactive group-containing water soluble macromers (available from Shearwater Polymers, Inc., Huntsville, Ala.) may be used, so long as the two reactive components can be dispersed within two separate phases.

Hydrogel microspheres also may be formed from non-polymerized hydrogel-forming materials that are stabilized by virtue of their limited solubility, ionic complexation or other means. More comprehensive listings of hydrogels suitable for use in the present invention are provided hereinabove. Other means to form the microdroplets that are precursors to the formation of the microspheres also may be used, for example, ultrasonic dispersion, spraying of the droplets, emulsion growth of small droplets, interfacial polymerization around the hydrophobic cores initiated by agents that are dispersed in the hydrophobic phase, etc.

Example 2

Fabrication of Targetable Microspheres

In addition to di-functional macromers, if semitelechelic macromers having free hydroxyl or carboxyl groups also are added to the aqueous phase, the resulting microspheres may be expected to have free functional groups available for further functionalization. If the dangling chain ends are selected from a mix of hydroxyl and carboxyl groups, separate activation schemes may be used to couple both carbohydrates and protein signaling sequences to the microspheres.

Mucins are carbohydrate molecules present on the surface of leukocytes and other white blood cells. These long chain molecules have a flexible nature and act as tethers for cell signaling molecules. These molecules, for example, allow leukocytes to identify target sites through their rolling action. Poly(ethylene oxide) molecules possess chain flexibility by virtue of their ether linkages and may be functionalized at their ends. Thus, these molecules may be used as tethers that bind cell signaling sequences at one end to the microsphere at the other end.

The microspheres described in Example 1 above may be functionalized with appropriate cell signaling or adhesion molecules that help guide the targeting of the microsphere upon intravascular administration. An injectable particle therefore may be prepared that includes a substance to be delivered and a polymer that is covalently bound to a biologically active molecule, preferably an antibody or antibody fragment, wherein the particle is prepared in such a manner that the biologically active molecule is on the outside surface of the particle. Injectable particles with antibody or antibody fragments on their surfaces thus may be used to target specific cells or organs as desired for the selective dosing of drugs.

Figure 3:
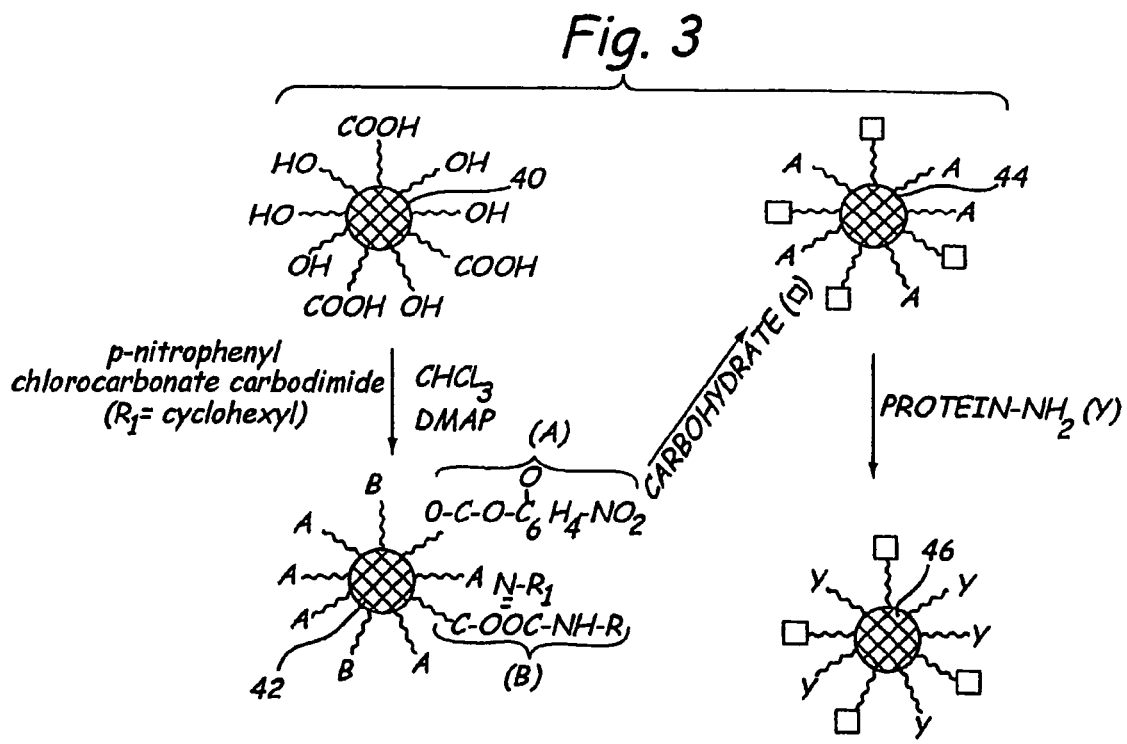
FIG. 3 illustrates steps of activating a hydrogel microsphere to enable the binding of cell-signaling carbohydrate and protein molecules to form targeted microspheres in accordance with the principles of the present invention.

Referring to FIG. 3, hydrogel microsphere 40 is first prepared in accordance with Example 1. Next, to couple carbohydrate and protein molecules, microsphere 40 is functionalized with a mix of dicyclohexyl carbodiimide (DCC), which reacts with the carboxyl groups, and p-nitrophenyl chlorocarbonate, which reacts with the hydroxyl groups, in a dry organic solvent (such as chloroform), to produce microsphere 42.

In a next step, coupling of a carbohydrate molecule of interest (such as L selectins or mucins) is performed in a basic aqueous environment (for example a 50 mM sodium borate buffer at pH 8.5) to produce intermediate microsphere 44. A final step of coupling a protein of interest (such as an antibody or an integrin) is performed, again in a basic aqueous environment, to produce targeted microsphere 46. The binding of proteins and carbohydrates may be evaluated by fluorescent immunocytochemical probes. The avidity of target molecule binding may be measured by competitive binding assays or radioimmunoassays.

The biologically active molecule, and in particular, an antibody or antibody fragment, may be covalently bound to the block copolymer by reaction with the terminal hydroxyl group of a poly(alkylene glycol) by any method known to those skilled in the art. For example, the hydroxyl group may be reacted with a terminal carboxyl group or terminal amino group on the molecule or antibody or antibody fragment, to form an ester or amide linkage, respectively.

Alternatively, the molecule may be linked to poly(alkylene glycol) through a difunctional spacing group such as a diamine or a dicarboxylic acid, including, but not limited to, sebacic acid, adipic acid, isophthalic acid, terephthalic acid, fumaric acid, dodecanedicarboxylic acid, azeleic acid, pimelic acid, suberic acid (octanedioic acid), itaconic acid, biphenyl-4,4'-dicarboxylic acid, benzophenone-4,4'-dicarboxylic acid, and p-carboxyphenoxyalkanoic acid. In these embodiments, the spacing group is reacted with a hydroxyl group on poly(alkylene glycol), and then reacted with the biologically active molecule.

As a further alternative, the spacing group can be reacted with a biologically active molecule or antibody or antibody fragment, and then reacted with a hydroxyl group on poly(alkylene glycol). The reaction should be accomplished under conditions that will not adversely affect the biological activity of the molecule being covalently attached to the nanoparticle. For example, conditions should be avoided that cause the denaturation of proteins or peptides, such as high temperature, certain organic solvents and high ionic strength solutions, when binding a protein to the particle. For example, organic solvents should be eliminated from the reaction system and a water soluble coupling reagent such as EDC should be used instead.

Physical and chemical attributes such as size, density, composition, receptor conjugate density, tether chain length etc. are expected to affect targeting behavior of these microspheres. The rolling behavior of these synthetic microspheres may be compared to that of leukocytes in a laminar flow chamber so as to evaluate their "targeting ability." Optimal targeting systems may then be combined with potential drug delivery approaches.

Example 3

Preparation of a Hydrogel Tablet

Eosin Y is illustratively chosen as a model water soluble drug, because it is freely soluble in water. 300 mg of Eosin Y may be mixed with 1 g of ethyl stearate and the mixture gently heated to 45° C. for 1 minute to allow the Eosin to dissolve and freely mix with the molten ethyl stearate. The mixture should be allowed to cool and crystallize. The mixture is then scraped from the container and transferred to a ball mill to grind the powder to a small particle size.

The ground powder should be sieved through a 100 mesh screen and the particles collected. 300 mg of such particles may be dispersed into a macromer solution prepared as follows. An acrylated copolymer of dl-lactic acid and poly(ethylene glycol) (PEG molecular weight 8,000 daltons, 10 moles of lactoic ester per mole of PEG) may be synthesized as described in the foregoing paper by Sawhney et al., and dissolved in a phosphate buffered solution at a pH of 7.4 and a concentration of 100 mg/mL. Irgacure 651 (Ciba Geigy) is dissolved in N-vinyl pyrrolidinone at a concentration of 600 mg/mL, and 5 μL of this initiator solution is added to 1 mL of the macromer solution under agitation. The mixture is pipetted to a 6 well dish and exposed to a long wave ultraviolet light at an intensity of 10 milliwatts/cm$^2$ for 1 minute to achieve gelation of the macromer.

Thus, a hydrogel tablet containing Eosin Y entrapped using a rate modifying agent (ethyl stearate) may be formed. The tablet may be placed in an aqueous solution to observe the release of Eosin Y, which is expected to be much slower and controlled compared to a tablet prepared in a similar fashion, but where the Eosin Y is not entrapped within ethyl stearate. No phase transfer agent is required in the fabrication of this drug delivery system.

While preferred illustrative embodiments of the invention are described above, it will be apparent to one skilled in the art that various changes and modifications may be made therein without departing from the invention, and it is intended in the appended claims to cover all such changes and modifications which fall within the true spirit and scope of the invention.

The invention claimed is:

1. A method of making a gel, the method comprising reacting one or more hydrophilic, synthetic macromers through covalent reactions to form a continuous, bioabsorbable, synthetic, covalently crosslinked hydrogel matrix in the presence of a hydrophobic material and a therapeutic agent, with a plurality of non-gaseous hydrophobic domains being formed from the hydrophobic material and dispersed in the continuous hydrogel matrix, with the therapeutic agent being associated with the hydrophobic domains.

2. The method of claim 1, wherein the hydrophobic material comprises a release rate modifying agent.

3. The method of claim 2, wherein the release rate modification agent is selected from the group consisting of capric acid, undecanoic, lauric acid, heneicosanoic, behenic acid, behenic acid ethyl ester, behenic acid methyl ester, tricosanoic acid, methyl ester tridecanoic acid, pentadecanoic acid, heptadecanoic acid, heptadecanoic, ethyl ester heptadecanoic, methyl ester nonadecanoic acid, myristic acid, myristic acid benzyl ester, myristic acid methyl ester, palmitic acid, palmitic acid benzyl ester, palmitic acid butyl ester, palmitic acid hexadecyl, palmitic acid methyl ester, palmitic acid myricyl ester, palmitic acid propyl ester, stearic acid, stearic acid benzyl ester, stearic acid butyl ester, stearic acid isobutyl ester, stearic acid cyclohexyl ester, stearic acid ethyl ester, stearic acid hexadecyl ester, stearic acid methyl ester, stearic acid 3-oxo ethyl ester, stearic acid 2-hydroxyethyl ester, stearic acid 6-oxo ethyl ester, stearic acid 10-oxo ethyl ester, stearic acid 12-oxy ethyl ester, stearic acid pentyl ester, stearic acid isopentyl ester, stearic acid phenyl ester, stearic acid isopropyl ester, and stearic acid tetrahydrofufuryl ester.

4. The method of claim 2, wherein the release rate modification agent is selected from the group consisting of fatty acids and triglycerides.

5. The method of claim 1 wherein the therapeutic agent has a molecular weight of less than 100,000.

6. The method of claim 2 wherein the therapeutic agent has a molecular weight less than 20,000.

7. The method of claim 1 wherein the therapeutic agent has a water solubility of greater than 0.01 mg/mL.

8. The method of claim 1 wherein the therapeutic agent is hydrophobic.

9. The method of claim 1 wherein the therapeutic agent is a member of the group consisting of a growth factor, a cytokine, an antimitotic drug, a radiation source, and an antineoplastic agent.

10. The method of claim 1 wherein the therapeutic agent is a member of the group consisting of antiallergenic agents, cardiovascular agents, agents affecting respiratory organs, hormones, agents affecting metabolism, and antimicrobial agents.

11. The method of claim 1 wherein the therapeutic agent is a member of the group consisting of chemotherapeutic agents, local anesthetics, antihistaminic, antiphlogistics, astringents, vitamins, antifungal agents, peripheral nervous anesthetics, vasodilators, anti-inflammatory agents, and immunosuppressants.

12. The method of claim 1, wherein the hydrophobic domains comprise microdroplets.

13. The method of claim 1, wherein the hydrophobic domains comprise microparticles.

14. The method of claim 1, wherein the hydrophobic domains comprise a compound having a melting point less than 65° C.

15. The method of claim 1 wherein the hydrophobic domains comprise surfactants.

16. The method of claim 1 wherein the hydrophobic domains are formed in situ as the hydrogel is formed from the macromers.

17. The method of claim 16 wherein the hydrophobic domains comprise micelles.

18. The method of claim 1 wherein the hydrophobic domains comprise the therapeutic agents.

19. The method of claim 1 wherein the hydrophobic domains have a size of from about 1 to about 10 microns.

20. The method of claim 1 further comprising forming the hydrogel matrix in-situ.

21. The method of claim 1 wherein one or more of the macromers comprise poly(ethylene glycol).

22. The method of claim 1 wherein one or more of the macromers further comprise a biodegradable portion.

23. The method of claim 1 wherein one or more of the macromers further comprise free functional groups that are free after the macromers are covalently crosslinked to form the hydrogel matrix.

24. The method of claim 1 wherein one or more of the macromers, before bonding, each comprise at least two electrophilic functional groups or at least two nucleophilic groups, and further comprising reacting the electrophilic functional groups with the nucleophilic groups in a covalent reaction to form the hydrogel matrix.

25. The method of claim 1, further comprising a binding ligand disposed within the hydrogel matrix.

* * * * *